United States Patent [19]

Bernstein

[11] 4,289,134

[45] Sep. 15, 1981

[54] TRIPOLAR CATHETER APPARATUS

[75] Inventor: Robert I. Bernstein, Tenafly, N.J.

[73] Assignee: Electro-Catheter Corporation, Rahway, N.J.

[21] Appl. No.: 59,523

[22] Filed: Jul. 23, 1979

[51] Int. Cl.³ .............................................. A61N 1/36
[52] U.S. Cl. .............................. 128/419 PG; 128/786
[58] Field of Search ....... 128/419 P, 419 PG, 419 PT

[56] References Cited

U.S. PATENT DOCUMENTS

| | | | |
|---|---|---|---|
| 3,478,746 | 11/1969 | Greatbatch | 128/419 PG |
| 3,614,955 | 10/1971 | Mirowski | 128/419 P |
| 3,625,201 | 12/1971 | Murphy, Jr. | 128/419 PT |
| 3,857,398 | 12/1974 | Rubin | 128/419 PG |

Primary Examiner—William E. Kamm
Attorney, Agent, or Firm—Hubbell, Cohen, Stiefel & Gross

[57] ABSTRACT

A tripolar catheter apparatus employing an automatic electronic switch is adapted for use with a conventional bipolar demand cardiac pacer for converting a bipolar pacing system into a tripolar pacing system in which stimulation can be applied between two intra-ventricular electrodes, such as ones located in the right ventricular apex, while sensing of ventricular depolarization may be obtained by an intra-ventricular apical electrode and an extra-ventricular electrode located outside the ventricle, such as in the right atrium or vena cava. The tripolar catheter apparatus comprises a pair of catheter terminals connected to the output terminals of the bipolar demand cardiac pacer and three output electrodes, namely a proximal electrode, a medial electrode and a distal electrode, which are provided to the heart. The distal electrode is the common electrode for both sensing and stimulation in the tripolar system while an automatic electronic switch selects either the proximal electrode or the medial electrode dependent on the provision of a cardiac stimulus from the pacer.

32 Claims, 4 Drawing Figures

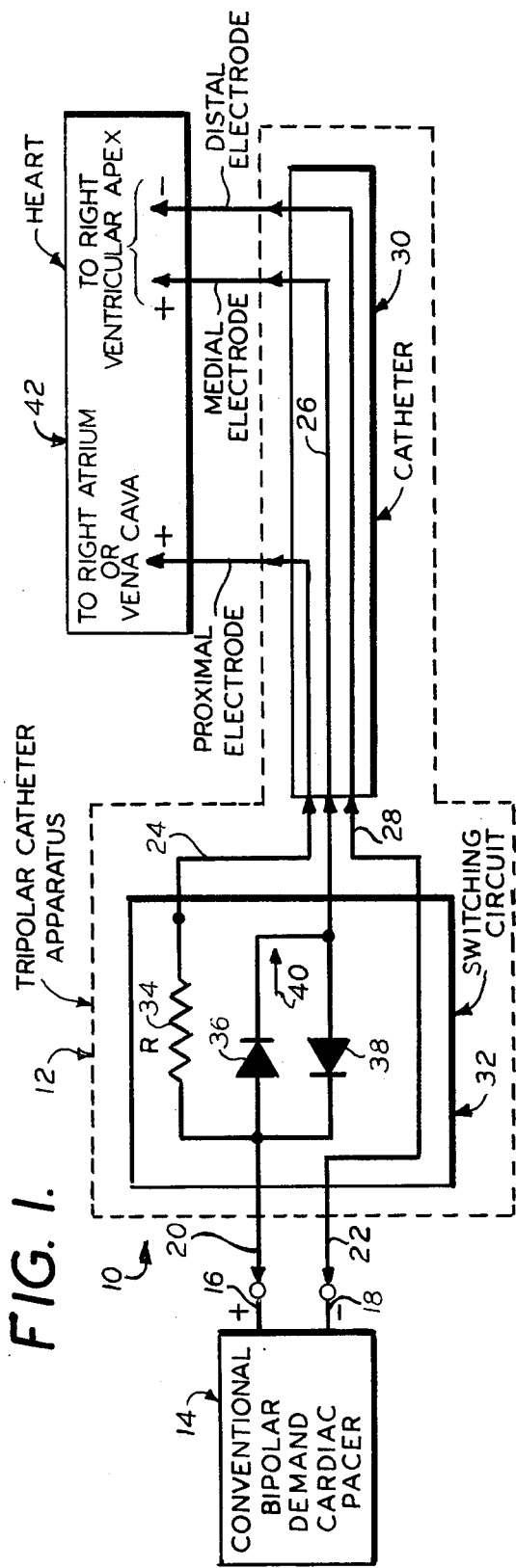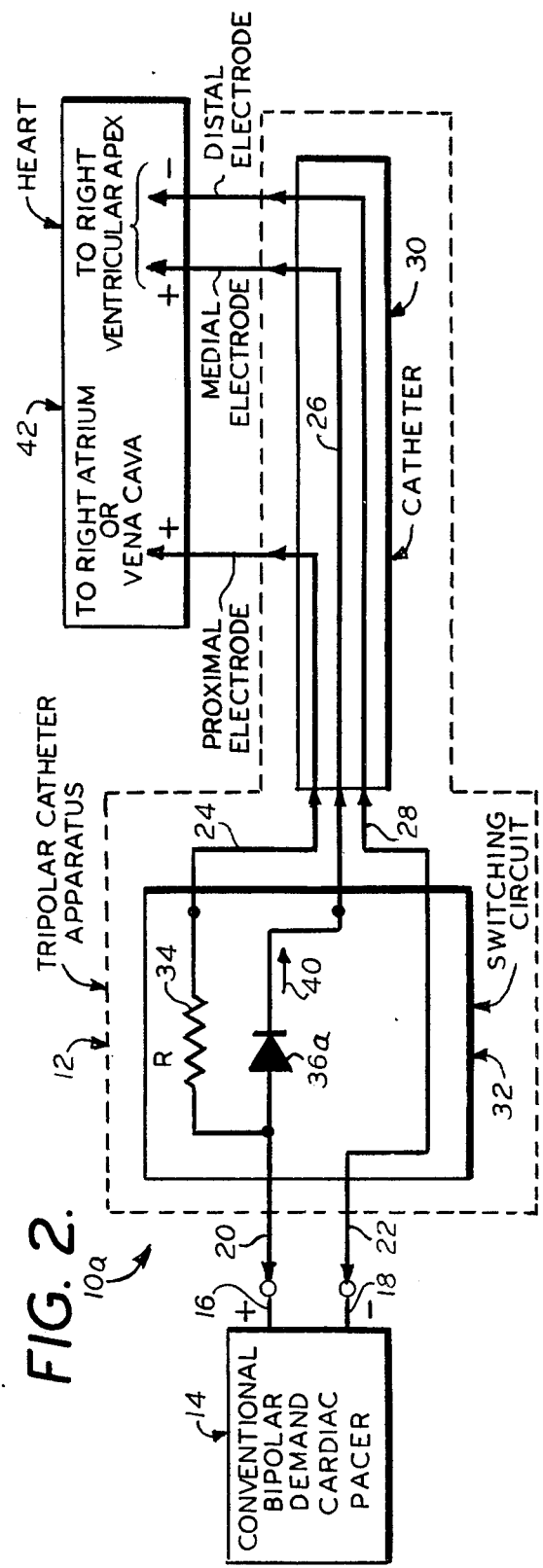

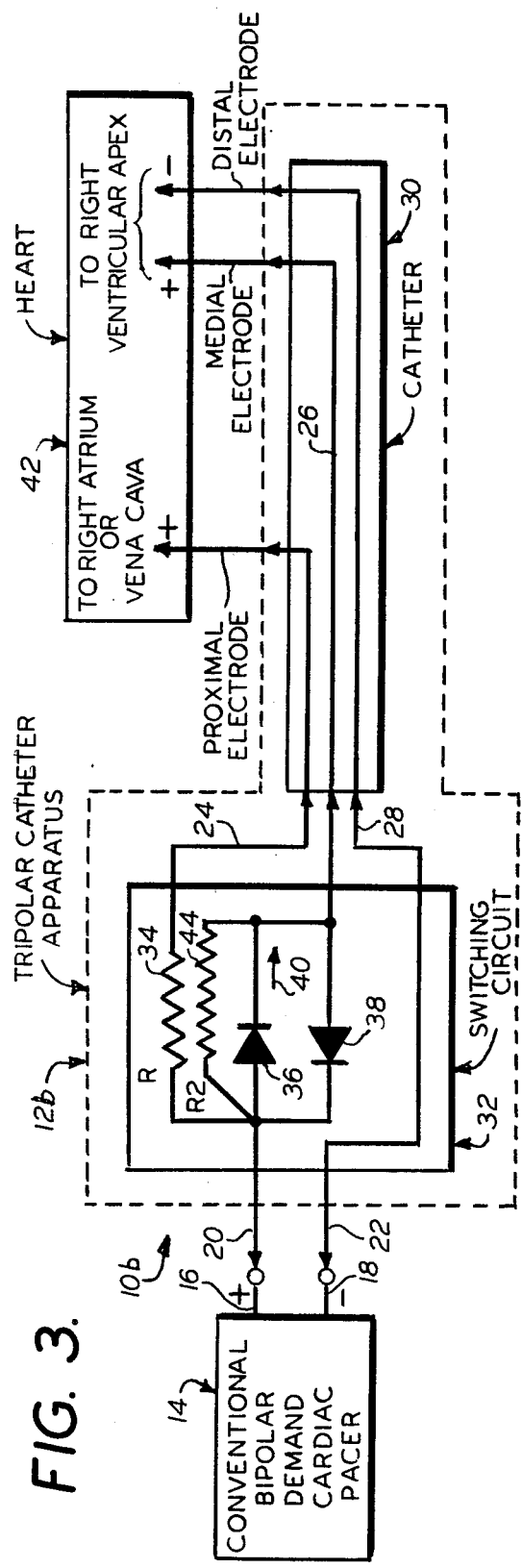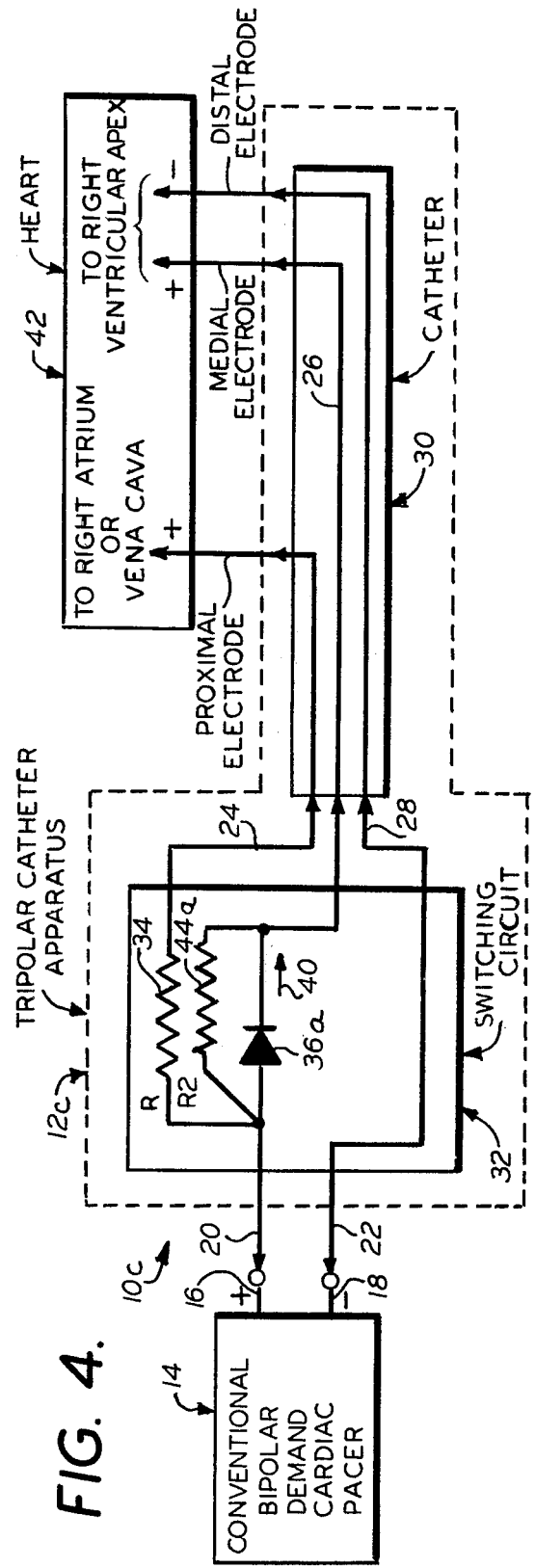

TRIPOLAR CATHETER APPARATUS

BACKGROUND OF THE INVENTION

1. Field of the Invention

The present invention relates to cardiac pacing systems and particularly to catheter apparatus usable in such cardiac pacing systems.

2. Description of the Prior Art

Bipolar pacing systems and particularly bipolar demand cardiac pacing systems in which a common pair of electrodes is employed for providing both stimulation and sensing of ventricular depolarization are well known. For example, such a bipolar demand cardiac pacing system is disclosed in U.S. Pat. Nos. 3,595,242; 3,478,746; 3,735,766, and my previous U.S. Pat. No. 3,908,667. Moreover, catheters for employment with such prior art cardiac pacing systems in which a predetermined spacing of the electrodes positioned in the heart is established by the catheter are also well known as disclosed, by way of example, in U.S. Pat. No. 3,915,174. However, with respect to the catheter disclosed in U.S. Pat No. 3,915,174, the resultant current flow may unintentionally involve the superior conduction system of the heart, in which instance, the cardiac pacer can induce undesirable ventricular arrhythmias, especially if the anode produces current through the super ventricular conduction system. The bipolar catheter disclosed in U.S. Pat. No. 3,915,174 recognizes this problem, however, it does not avoid stimulation of the super ventricular conductive system but, rather, merely makes an effort to minimize such stimulation by employing a large electrode in order to obtain a low current density. Thus, the problem may still occur.

As set forth in my previous U.S. Pat. No. 3,908,667, there are several disadvantages to such bipolar demand cardiac pacing which can be overcome by providing a tripolar demand cardiac pacing system, such as the system shown in FIG. 7 of that patent. Thus, in a tripolar demand cardiac pacing system, stimulation is applied between a pair of intra-ventricular electrodes whereas sensing of ventricular depolarization is obtained between an intra-ventricular electrode and an extra-ventricular electrode. The advantage of sensing between an intra-ventricular and an extra-ventricular electrode is that this pair of electrodes spans the entire ventricle and, therefore, receives the maximum ventricular depolarization signal, whereas the conventional bipolar arrangement of sensing between two closely adjacent electrodes located within the ventricle may result in failure to detect ventricular depolarization because the geometry of the depolarization wave front under certain conditions may not produce a sufficient voltage difference between such adjacent electrodes. Such a failure to sense a spontaneous depolarization would result in the demand cardiac pacer's reversion to the free running mode, with the danger of an electronic stimulus applied during this vulnerable period causing fibrillation. Even if such fibrillation does not occur, competition between the spontaneous cardiac cycle and the electronic cardiac stimulus may cause the aforementioned harmful arrhythmias. As was previously mentioned, stimulation applied between the extra-ventricular and intra-ventricular electrodes can present some danger in that the current through the extra-ventricular electrode may stimulate the upper conduction system consisting of the sino-atrial node, the atrio-ventricular node, and the conduction pathways between them. Such simultaneous stimulation of both the extra-ventricular and ventricular conduction systems departs substantially from the natural sequence of the heart and can cause undesirable results.

The tripolar arrangement described with reference to FIG. 7 of my aforementioned previous U.S. Pat. No. 3,908,667 overcomes several of these problems inherent in a bipolar cardiac demand pacing system. However, such a system as disclosed therein involves circuit redesign. Moreover, in certain instances, the physician may still wish to use bipolar cardiac demand pacing initially with subsequent conversion to tripolar cardiac demand pacing if certain problems arise. Applicant is presently unaware of any available prior art cardiac pacing systems which enable a conventional bipolar demand cardiac pacer to be employed as a tripolar demand cardiac pacer when the advantages of such tripolar demand cardiac pacing are desired. These disadvantages of the prior art are overcome by the present invention.

SUMMARY OF THE INVENTION

An improved cardiac pacing system and a tripolar catheter apparatus adapted for use with a bipolar demand cardiac pacer in such a system. The bipolar demand cardiac pacer has a common pacer terminal pair for providing both cardiac depolarization sensing and cardiac stimulation in a human patient dependent on the mode of the pacer with sensing being provided in a sensing mode and stimulation being provided in a stimulation mode. The catheter is further adapted for insertion through a portion of the patient's circulatory system into the heart. The aforementioned catheter apparatus comprises a first catheter terminal connectable to one pacer terminal of the pacer common terminal pair, and a second catheter terminal connectable to the other pacer terminal of the pacer common terminal pair. In addition, the tripolar catheter apparatus includes a first proximal electrode, a second medial electrode, a third distal electrode, and switch means responsive to the provision of a cardiac stimulus from the pacer. The switch means is connected between the first catheter terminal and the medial and proximal electrodes for selecting either the medial or proximal electrode dependent on the provision of the cardiac stimulus from the pacer. The distal electrode is substantially directly connectable to the other catheter terminal irrespective of the selection of the medial or distal electrode. The distal and medial electrodes are adapted for use as intra-ventricular electrodes, such as ones locatable in the right ventricular apex, whereas the proximal electrode is adapted for use as an extra-ventricular electrode, such as one locatable outside the ventricle in the right atrium or vena cava.

The switch means is responsive to the provision of the cardiac stimulus from the pacer in the pacer stimulating mode for providing the stimulus to the heart between the intra-ventricular distal and medial electrodes during the presence of such cardiac stimulus. In addition, the switch means is responsive to the pacer sensing mode for providing depolarization sensing from the heart between the intra-ventricular distal electrode and the extra-ventricular proximal electrode. In this manner a bipolar demand cardiac pacer is usable as a tripolar demand cardiac pacer. The aforementioned switch means may comprise a bidirectional diode switch means, such as a pair of parallel connected diodes having their respective polarities reversed so as to make the tripolar catheter apparatus function independently of the polarity of the connection of the catheter terminals to the conventional bipolar cardiac demand pacer terminals. In addition, a first resistive impedance R is preferably provided between the proximal electrode and the first catheter terminal in parallel with the diode switch and a physiological impedance $z_p$ is providable between the proximal and distal electrodes when the catheter apparatus is connected to the heart. In addition, the cardiac pacer has an associated input impedance $z_i$ and the resistive impedance R is preferably related to the distal-proximal electrode physiological impedance $z_p$ in the pacer stimulating mode in accordance with a voltage divider ratio of $Z_p/R+Z_p$ when the cardiac stimulus is present at the first catheter terminal and is related to the cardiac pacer input $z_i$ in the pacer sensing mode in accordance with the voltage divider ratio $Z_i/R+Z_i$, where $Z_p<R<Z_i$. If desired, a second resistive impedance $R_2$ may be connected in parallel with the aforementioned diode switch for providing a high impedance leakage current path in the opposite direction to the normal direction of current flow to the medial electrode to alleviate any non-zero DC polarization of the medial electrode should it occur.

BRIEF DESCRIPTION OF DRAWINGS

FIG. 1 is a schematic diagram, partially in block, of the preferred embodiment of the tripolar catheter apparatus and improved cardiac pacing system of the present invention;

FIG. 2 is a schematic diagram, partially in block, similar to FIG. 1, of an alternative embodiment of the tripolar catheter apparatus and improved cardiac pacing system shown in FIG. 1;

FIG. 3 is a schematic diagram, partially in block, similar to FIG. 1, of another alternative embodiment of the arrangement shown in FIG. 1; and FIG. 4 is a schematic diagram, partially in block, of an alternative arrangement of the embodiment shown in FIG. 2.

DETAILED DESCRIPTION OF THE PREFERRED EMBODIMENTS

Referring now to the drawings in detail, and initally to FIG. 1 thereof, the improved cardiac pacing system of the present invention, generally referred to by the reference numeral 10, employing the preferred tripolar catheter apparatus of the present invention, generally referred to by the reference numeral 12, is shown. The improved cardiac pacing system 10 of the present invention is preferably a tripolar demand cardiac pacing system in which a conventional bipolar demand cardiac pacer 14 may be usable as a tripolar demand cardiac pacer. The bipolar demand cardiac pacer 14 illustrated in FIG. 1, and similarly illustrated in FIGS. 2 through 4, is a conventional one, such as the type of bipolar demand cardiac pacer described in my previous U.S. Pat. No. 3,908,667. In such a conventional bipolar demand cardiac pacing system, electronic stimulation of the heart is applied between a pair of terminals 16 and 18, such as through a conventional bipolar catheter, which are located closely adjacent to each other within the ventricle of the heart. Moreover, these same terminals 16 and 18 are also used in a conventional bipolar demand cardiac pacing system for sensing ventricular depolarization. For purposes of illustration, pacer terminal 16 of this common terminal pair 16–18 in FIG. 1 is labeled as the anode and pacer terminal 18 is labeled as the cathode.

As shown and preferred in FIG. 1, the improved cardiac pacing system 10 of the present invention is a tripolar demand cardiac pacing system even though a conventional bipolar demand cardiac pacer 14 is used to provide the cardiac stimulating signal. In order to accomplish this, the preferred tripolar catheter apparatus 12 of the present invention is employed with the conventional bipolar demand cardiac pacer 14. The tripolar catheter apparatus 12 preferably includes a pair of catheter terminals 20 and 22 which are respectively connected to the anode 16 and the cathode 18 comprising the common terminal pair of the conventional bipolar demand cardiac pacer 14. As is also shown and preferred in FIG. 1, the tripolar catheter apparatus 12 also comprises three electrodes labeled, respectively, the proximal electrode 24, the medial electrode 26 and the distal electrode 28 which are provided in a conventional catheter sheathing 30.

As further shown and preferred in FIG. 1, the catheter terminals 20 and 22 are interconnected to the electrodes 24, 26, and 28 through an automatic switching circuit 32. As shown and preferred in FIG. 1, this switching circuit 32 preferably comprises a bidirectional switch, as will be described in greater detail hereinafter, in order to enable the tripolar catheter apparatus 12 to operate successfully irrespective of the polarity of the connection of the catheter terminals 20 and 22 to the pacer terminals 16 and 18 of the bipolar demand cardiac pacer 14. The switching circuit portion 32 of the tripolar catheter apparatus 12 preferably includes a resistive impedance 34, labeled "r", between the proximal electrode 24 and the catheter terminal 20 which is connected to the anode 16 of the bipolar demand cardiac pacer 14. As will be described in greater detail hereinafter, the value of "R" 34 is small compared to the input impedance $Z_i$ of the bipolar demand cardiac pacer 14, which input impedance is normally approximately 100,000 ohms or greater, seen by the depolarization signal applied to the pacer 14 that must be conventionally sensed for the purpose of inhibiting the emission of an electronic stimulus from the pacer 14. In addition, the value of "R" 34 is preferably large compared to the physiological impedance $Z_p$, which is normally approximately 500 ohms, between the proximal 24 and distal 30 electrodes.

As also shown and preferred in FIG. 1, switch 32 also includes a pair of conventional diodes 36 and 38, such as conventional silicon diodes, such as Fairchild FD333 silicon diodes or conventional "hot carrier" diodes such as the type available from Hewlett Packard, connected in parallel between catheter terminal 20 and the medial electrode 26. The normal direction of current flow in the system 10 is indicated by arrow 40 in FIG. 1 and, as shown and preferred in FIG. 1, the polarity of diode 38 is opposite to the polarity of diode 36; that is, the anode of diode 38 is connected to the cathode of diode 36 and the cathode of diode 38 is connected to the anode of diode 36. In this manner, a bidirectional switch 32 is provided, as will be described in greater detail hereinafter. Furthermore, as shown and preferred in FIG. 1, the proximal electrode 24 is preferably locatable in the atrium or vena cava of the heart 42 and comprises an extra-ventricular electrode whereas the medial electrode 26 and the distal electrode 30 are preferably locatable in the right ventricular apex of the heart 42 and comprise a pair of intra-ventricular electrodes.

Now describing the operation of the improved tripolar cardiac pacing system 10 of the present invention and the preferred tripolar catheter apparatus 12 usable therein. During the presence of a conventionally generated electronic stimulus to the heart 42 from the conventional bipolar demand cardiac pacer 14, which stimulus is present between the pacer anode 16 and cathode 18, diode 36 conducts the forward resistance of the diodes 36 and 38 preferably being less than 100 ohms for conventional pacer stimulation currents. In the preferred bidirectional diode switch 36–38 arrangement illustrated in FIG. 1, because of the polarity of diode 38 being opposite to the polarity of diode 36, only one of the diodes 36 or 38 conducts in response to the presence of the pacer provided electronic stimulus, the diode which conducts being dependent on the polarity of the connection of catheter terminals 20 and 22 to the pacer electrodes 16 and 18. Thus, in the arrangement shown in FIG. 1, wherein catheter terminal 20 is connected to the anode 16 and catheter terminal 22 is connected to the cathode 18, diode 36 will conduct in response to the presence of the aforementioned pacer provided electronic stimulus and diode 38 will remain cut off. However, if, instead, the polarity of the connections shown were reversed and catheter terminal 20 were instead connected to cathode 18 and catheter terminal 22 were instead connected to anode 16, diode 38 would then conduct in response to the presence of the pacer provided electronic stimulus and diode 36 would remain cut off. Apart from this, the operation of the tripolar catheter appartus 12 is identical in either instance thus enabling the tripolar catheter apparatus 12 to operate successfully irrespective of the polarity of the connections of the catheter terminals 22 and 22 to the pacer terminals 16 and 18. When the diode, diode 36 in the example shown in FIG. 1, conducts in response to the presence of the pacer provider electronic stimulus between catheter terminals 20 and 22, this stimulus is then applied between the distal 28 and medial 26 electrodes to the heart 42, with the current passing in the direction indicated by arrow 40 through the medial electrode 26 to the heart 42.

Because resistive impedance "R" 34 is preferably large compared to the physiological impedance $Z_p$ between the distal 28 and proximal 24 electrodes, only a small insignificant fraction of the pacer provided electronic stimulus appears between the distal 28 and proximal 24 electrodes, the fraction being dependent on a voltage divider relationship so that the larger the ratio between the resistive impedance "R" 34 and the distal-proximal physiological impedance $Z_p$, the smaller the fractional portion of the stimulus appearing between the distal 28 and proximal 24 electrodes will be. Thus, the preferred voltage divider ratio for the stimulating mode of the pacer 14 is defined by the expression $Z_p/R + Z_p$ when the cardiac stimulus is present between the catheter terminals 20 and 22 with the distal-proximal physiological impedance $Z_p$, as previously mentioned, being small as compared to the resistive impedance "R" 34. Thus, by way of example, if the value of "R" 34 is chosen as 10,000 ohms and the physiological impedance $Z_p$ is approximately 500 ohms, then the aforementioned voltage divider ratio defining the fraction or percentage of the pacer 14 provided stimulus which would appear between the distal 28 and proximal 24 electrodes would be equal to 1/21 or approximately 4.76%, which is substantially equal to 5%. Preferably, this voltage divider ratio of the fraction or percentage of the pacer 14 provided stimulus appearing between the distal 28 and proximal 24 electrodes may be in the range of 4% to 25%, with it presently most preferably being the aforementioned substantially 5%.

In the absence of an electronic stimulus from bipolar demand cardiac pacer 14 between pacer terminals 16 and 18, which is defined as the sensing mode of the conventional demand pacer 14, the previously described stimulating condition being defined as the stimulation mode of pacer 14, both diodes 36 and 38 are cut off and the ventricular depolarization wave form is then conventionally conveyed to the pacer terminals 16 and 18 with negligible attenuation through the proximal electrode 24, back through the resistive impedance "R" 34 to catheter terminal 20 and therefrom to pacer terminal 16, and through distal electrode 28 to catheter terminal 22 and back to pacer terminal 18. This is so because the resistive impedance "R" 34 is preferably selected to be much less than the pacer 14 input impedance $Z_i$. Moreover, the connection between distal electrode 28 and catheter terminal 22 is preferably accomplished via a zero or low resistance conductor, such as preferably one having a resistance of less than 10 ohms. Diodes 36 and 38 are, thus, cut off in this sensing mode condition in which an electronic stimulus is not provided from pacer 14 because the voltages produced physiologically between the various electrodes are normally less than 50 millivolts with the physiological potentials therefor being insufficient to bring a conventional solid state diode of the type preferably utilized for diodes 36 and 38 into conduction. Accordingly, diodes 36 and 38 will not turn on or conduct in this condition. Thus, as previously mentioned, the ventricular depolarization voltage present between the distal 28 and proximal 24 electrodes will be conducted back through the resistive impedance "R" 34 to the pacer terminals 16 and 18. Once again, a voltage divider relationship or ratio is established which determines the percentage of this ventricular depolarization voltage provided between the distal 28 and proximal 24 electrodes which will appear between the pacer 14 terminals 16 and 18. Preferably, as long as the pacer 14 input impedance $Z_i$ is large compared to the selected resistive impedance "R" 34, such as on the order of magnitude of 10:1, most of the ventricular depolarization voltage present between the distal 28 and proximal 24 electrodes will appear between the pacer 14 terminals 16 and 18. This voltage divider ratio which defines the fraction or percentage of the ventricular depolarization voltage present between the distal 28 and proximal 24 electrodes which subsequently appears between the pacer 14 terminals 16 and 18 is defined by the expression $Z_i/R + Z_i$ for the sensing mode of the pacer 14, the previously described voltage divider ratio $Z_p/R + Z_p$ relating to the stimulating mode of the pacer 14. Thus, assuming the resistive impedance "R" 34, by way of example, is 10,000 ohms and the input impedance $Z_i$ of the conventional bipolar demand cardiac pacer 14 chosen is 100,000 ohms, as in the previous example, then this voltage divider ratio would be equal to 10/11 or approximately 90.9%, which is substantially equal to 90%. Preferably, this voltage divider ratio may be in the range of approximately 80% to substantially 100%, with it presently most preferably being the aforementioned substantially 90%. Thus, as stated above, the resistive impedance "R" 34 is preferably selected so as to be small compared to the conventional pacer 14 input impedance $Z_i$ and large compared to the physiological impedance $Z_p$ present between the distal 28 and proximal 24 electrodes, this relationship being represented by the expression $Z_p < R < Z_i$. In addition, as previously stated above, in the preferred embodiment of FIG. 1, the polarity of the medial 26 and distal 28 electrodes relative to each other is reversable merely by reversing the connection of the catheter terminals 20 and 22 to the two pacer 14 terminals 16 and 18, such reversal not interfering with the operation of the preferred tripolar catheter apparatus 12 or the overall improved cardiac pacing system 10.

Referring now to FIG. 2, an alternative embodiment of the improved cardiac pacing system 10 and tripolar catheter apparatus 12 illustrated in FIG. 1 is shown with like functioning components having the identical reference numerals. Moreover, the only difference between the system disclosed in FIG. 2 and that described with reference to FIG. 1 is that only a single diode 36a is employed between catheter terminal 20 and the medial electrode 26 as opposed to the opposite polarity connected diode pair 36-38, with diode 36a, however, preferably being identical in function and operation to diode 36. The operation of the tripolar catheter apparatus 12a illustrated in FIG. 2 is identical to that previously described with reference to the tripolar catheter apparatus 12 of FIG. 1 with the exception that careful attention must be paid to the proper polarity connection of the catheter terminal 20 to the anode 16 of pacer 14 since the arrangement 12a illustrated in FIG. 2 is not bidirectional. Thus,, if catheter terminal 20 is instead connected to the cathode 28, then the arrangement 12a of FIG. 2 will not operate properly since diode 36a will not then be placed into conduction in the stimulating mode of pacer 14 nor will it be placed into conduction in the sensing mode. Apart from this difference, the aforementioned voltage divider ratios described with reference to FIG. 1 as well as the balance of the operation of the tripolar catheter apparatus 12a and the cardiac pacing system 10a is preferably identicial to that described with reference to tripolar catheter apparatus 12 and cardiac pacing system 10 and will not be described in greater detail hereinafter.

Referring now to FIG. 3, an alternative embodiment of the cardiac pacing system 10 and tripolar catheter apparatus 12, given reference numerals 10b and 12b, respectively, is shown. Cardiac pacing system 10b and tripolar catheter apparatus 12b are preferably identical in function and operation to that described with reference to FIG. 1, with like reference numerals being used for identical components, with the exception of the provision of an additional resistance labeled "R2", given reference numeral 44, connected in parallel with diode pair 36-38 in order to provide a high impedance leakage current path in the opposite direction to the normal direction of current flow, indicated by arrow 40. Since the current normally passes in only one direction through the medial electrode 26, which direction is indicated by arrow 40, non-zero DC polarization of the medial electrode 26 could possibly occur. Resistive impedance "R2" 44, which provides a high impedance leakage current path in the opposite direction to the normal direction of current flow indicated by arrow 40, is preferably provided to alleviate such non-zero DC polarization of the medial electrode 26 if it should occur. Accordingly, if such non-zero DC polarization is not a problem or a concern, resistive impedance "R2" 44 may be omitted. However, in the event such resistive impedance "R2" 44 is provided, then preferably the value of resistive impedance "R2" 44 is greater than or equal to twice the selected value of the resistive impedance "R" 34.

Referring now to FIG. 4, an alternative embodiment of the cardiac pacing system 10a and tripolar catheter apparatus 12a illustrated in FIG. 2, generally referred to by reference numerals 10C and 12c, respectively, is shown. The only difference in operation and function of the cardiac pacing system 10c and tripolar catheter apparatus 12c illustrated in FIG. 4 from that of cardiac pacing system 10a and tripolar catheter apparatus 12a is in the provision of the aforementioned parallel connected second resistive impedance "R2" employed in the embodiment of FIG. 3 and given like reference numeral 44a, which functions and operates in the same manner as resistive impedance "R2" 44 to provide a high impedance leakage current path in the opposite direction to the normal direction of current flow indicated by arrow 40 to alleviate the aforementioned non-zero DC polarization of the medial electrode 26 if it should occur. As previously mentioned, if such polarization is not a problem or a concern, resistive impedance "R2" 44a may be omitted. If, however, it is employed, then preferably the value of resistive impedance "R2" 44a, whose function is identical to resistive impedance "R2" 44, is greater than or equal to twice the selected value of the resistive impedance "R" 34.

It is to be understood that the above described embodiments of the invention are merely illustrative of the principles thereof and that numerous modifications and embodiments of the invention may be derived within the spirit and scope thereof.

What is claimed is:

1. A tripolar catheter apparatus connectable to a bipolar demand cardiac pacer having a common pacer terminal pair for providing both cardiac depolarization sensing and cardiac stimulation in a human patient dependent on the mode of said pacer, said sensing being provided in a sensing mode and said stimulation being provided in a stimulation mode, said catheter being insertable through a portion of the patient's curculatory system into the heart, said tripolar catheter apparatus comprising a first catheter terminal connected to one pacer terminal of said pacer common terminal pair, a second catheter terminal connected to the other pacer terminal of said pacer common terminal pair, a first proximal electrode, a second medial electrode, a third distal electrode and switch means responsive to the provision of a cardiac stimulus from said pacer, said switch means being connected between said first catheter terminal and said medial and proximal electrodes for selecting either said medial or proximal electrode dependent on the provision of said cardiac stimulus from said pacer, said distal electrode being connected to said other catheter terminal irrespective of said selection of said medial or distal electrode, said distal and medial electrodes comprising intra-ventricular electrodes, said proximal electrode comprising an extra-ventricular electrode, said switch means being responsive to the provision of said cardiac stimulus from said pacer in said pacer stimulating mode for providing said stimulus to the heart between said intra-ventricular distal and medial electrodes during the presence of said cardiac stimulus, said switch means being responsive to said pacer sensing mode for providing said depolarization sensing from the heart between said intra-ventricular distal electrode and said extra-ventricular proximal electrode, whereby said bipolar demand cardiac pacer is usable as a tripolar demand cardiac pacer.

2. A tripolar catheter apparatus in accordance with claim 1 wherein said medial electrode is connected in parallel to said proximal electrode through a diode switch means, said diode switch means being conductive in response to the presence of said cardiac stimulus at said first catheter terminal for providing said cardiac stimulus between said medial and distal electrodes.

3. A tripolar catheter apparatus in accordance with claim 2 wherein a first resistive impedance R is connected between said proximal electrode and said first catheter terminal, a physiological impedance $Z_p$ being present between said proximal and distal electrodes when said catheter apparatus is connected to the heart, and said cardiac pacer has an associated input impedance $Z_i$ with said resistive impedance R being related to said physiological impedance $Z_p$ in accordance with a voltage divider ratio of $Z_p/(R+Z_p)$ when said cardiac stimulus is present at said first catheter terminal, where $Z_p < R$.

4. A tripolar catheter apparatus in accordance with claim 3 wherein in said pacer sensing mode, said resistive impedance R is further related to said cardiac pacer input impedance $Z_i$ in accordance with a voltage divider ratio of $Z_i/(R+Z_i)$, where $Z_p < R < Z_i$.

5. A tripolar catheter apparatus in accordance with claim 4 wherein the value of the ratio $Z_p/(R+Z_p)$ is in the range of 4% to 25%.

6. A tripolar catheter apparatus in accordance with claim 5 wherein the value of the ratio $Z_p/(R+Z_p)$ is substantially equal to 5%.

7. A tripolar catheter apparatus in accordance with claim 5 wherein the value of the ratio $Z_i/(R+Z_i)$ is in the range of 80% to substantially 100%.

8. A tripolar catheter apparatus in accordance with claim 7 wherein the value of the ratio $Z_i/(R+Z_i)$ is substantially equal to 90%.

9. A tripolar catheter apparatus in accordance with claim 8 wherein the value of the ratio $Z_p/(R+Z_p)$ is substantially equal to 5%.

10. A tripolar catheter apparatus in accordance with claim 4 wherein the value of the ratio $Z_i/(R+Z_i)$ is in the range of 80% to substantially 100%.

11. A tripolar catheter apparatus in accordance with claim 2 wherein said diode switch means comprises a bidirectional diode switch means conductive in response to the presence of said cardiac stimulus at said first catheter terminal irrespective of the polarity of said first catheter terminal.

12. A tripolar catheter apparatus in accordance with claim 11 wherein said bidirectional diode switch means comprises a pair of diodes connected in parallel with opposite polarities.

13. A tripolar catheter apparatus in accordance with claim 12 wherein said bidirectional diode switch means further comprises a second resistive impedance $R_2$ connected in parallel with said parallel connected diode pair for providing a high impedance leakage current path in the opposite direction to the normal direction of current flow to said medial electrode.

14. A tripolar catheter apparatus in accordance with claim 2 wherein said diode switch means comprises at least a first diode and a resistive impedance $R_2$ connected in parallel with said first diode for providing a high impedance leakage current path in the opposite direction to the normal direction of current flow to said medial electrode.

15. A tripolar catheter apparatus in accordance with claim 14 wherein another resistive impedance R is provided between said proximal electrode and said first catheter terminal, the value of said resistive impedance $R_2$ being at least twice the value of said other resistive impedance R.

16. A tripolar catheter apparatus in accordance with claim 1 wherein a first resistive impedance R is connected between said proximal electrode and said first catheter terminal, a physiological impedance $Z_p$ being present between said proximal and distal electrodes when said catheter apparatus is connected to the heart, and said cardiac pacer has an associated input impedance $Z_i$ with said resistive impedance R being related to said distal-proximal electrode physiological impedance $Z_p$ in accordance with a voltage divider ratio of $Z_p/(R+Z_p)$ when said cardiac stimulus is present at said first catheter terminal, where $Z_p < R$.

17. A tripolar catheter apparatus in accordance with claim 16 wherein in said pacer sensing mode, said resistive impedance R is further related to said cardiac pacer input impedance $Z_i$ in accordance with a voltage divider ratio of $Z_i/(R+Z_i)$, where $Z_p < R < Z_i$.

18. A tripolar catheter apparatus in accordance with claim 17 wherein the value of the ratio $Z_i/(R+Z_i)$ is in the range of 80% to substantially 100%.

19. A tripolar catheter apparatus in accordance with claim 16 wherein the the value of the ratio $Z_p/(R+Z_p)$ is in the range of 4% to 25%.

20. A tripolar catheter apparatus in accordance with claim 19 wherein the value of the ratio $Z_i/(R+Z_i)$ is in the range of 80% to substantially 100%.

21. A tripolar catheter apparatus in accordance with claim 1 wherein said first catheter terminal is an anode and said second catheter terminal is a cathode.

22. In a cardiac pacing system comprising a bipolar demand cardiac pacer having a common pacer terminal pair for providing both cardiac depolarization sensing and cardiac stimulation in a human patient dependent on the mode of said pacer, said sensing being provided in a sensing mode and said stimulation being provided in a stimulation mode, and a catheter means insertable through a portion of the patient's circulatory system into the heart, the improvement comprising a tripolar catheter apparatus as said catheter means, said tripolar catheter apparatus comprising a first catheter terminal connected to one pacer terminal of said pacer common terminal pair, a second catheter terminal connected to the other pacer terminal of said pacer common terminal pair, a first proximal electrode, a second medial electrode, a third distal electrode and switch means responsive to the provision of a cardiac stimulus from said pacer, said switch means being connected between said first catheter terminal and said medial and proximal electrodes for selecting either said medial or proximal electrode dependent on the provision of said cardiac stimulus from said pacer, said distal electrode being connected to said other catheter terminal irrespective of said selection of said medial or distal electrode, said distal and medial electrodes comprising intra-ventricular electrodes, said proximal electrode comprising an extra-ventricular electrode, said switch means being responsive to the provision of said cardiac stimulus from said pacer in said pacer stimulating mode for providing said stimulus to the heart between said intra-ventricular distal and medial electrodes during the presence of said cardiac stimulus, said switch means being responsive to said pacer sensing mode for providing said depolarization sensing from the heart between said intra-ventricular distal electrode and said extra-ventricular proximal electrode, whereby a tripolar demand cardiac pacing system is provided.

23. An improved cardiac pacing system in accordance with claim 22 wherein said medial electrode is connected in parallel to said proximal electrode through a diode switch means, said diode switch means being conductive in response to the presence of said cardiac stimulus at said first catheter terminal for providing said cardiac stimulus between said medial and distal electrodes.

24. An improved cardiac pacing system in accordance with claim 23 wherein a first resistive impedance R is connected between said proximal electrode and said first catheter terminal, a physiological impedance $Z_p$ being present between said proximal and distal electrodes when said catheter apparatus is connected to the heart, and said cardiac pacer has an associated input impedance $Z_i$ with said resistive impedance R being related to said physiological impedance $Z_p$ in accordance with a voltage divider ratio of $Z_p/(R+Z_p)$ when said cardiac stimulus is present at said first catheter terminal, where $Z_p < R$.

25. An improved cardiac pacing system in accordance with claim 24 wherein in said pacer sensing mode, said resistive impedance R is further related to said cardiac pacer input impedance $Z_i$ in accordance with a voltage divider ratio of $Z_i/(R+Z_i)$, where $Z_p < R < Z_i$.

26. An improved cardiac pacing system in accordance with claim 25 wherein the value of the ratio $Z_p/(R+Z_i)$ is in the range of 4% to 25%.

27. An improved cardiac pacing system in accordance with claim 26 wherein the value of the ratio $Z_i/(R+Z_i)$ is in the range of 80% to substantially 100%.

28. An improved cardiac pacing system in accordance with claim 25 wherein the value of the ratio $Z_i/(R+Z_i)$ is in the range of 80% to substantially 100%.

29. An improved cardiac pacing system in accordance with claim 23 wherein said diode switch means comprises a bidirectional diode switch means conductive in response to the presence of said cardiac stimulus at said first catheter terminal irrespective of the polarity of said first catheter terminal.

30. An improved cardiac pacing system in accordance with claim 29 wherein said bidirectional diode switch means comprises a pair of diodes connected in parallel with opposite polarities.

31. An improved cardiac pacing system in accordance with claim 30 wherein said bidirectional diode switch means further comprises a second resistive impedance $R_2$ connected in parallel with said parallel connected diode pair for providing a high impedance leakage current path in the opposite direction to the normal direction of current flow to said medial electrode.

32. An improved cardiac pacing system in accordance with claim 23 wherein said diode switch means comprises at least a first diode and a second resistive impedance $R_2$ connected in parallel with said first diode for providing a high impedance leakage current path in the opposite direction to the normal direction of current flow to said medial electrode.

* * * * *